United States Patent
Endoh et al.

(10) Patent No.: US 7,709,690 B2
(45) Date of Patent: May 4, 2010

(54) METHOD FOR PRODUCING TERTIARY BUTYL ALCOHOL

(75) Inventors: Tohru Endoh, Hatsukaichi (JP); Shigeho Tanaka, Otake (JP); Haruki Sato, Hatsukaichi (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 362 days.

(21) Appl. No.: 11/721,742

(22) PCT Filed: Dec. 15, 2005

(86) PCT No.: PCT/JP2005/023047

§ 371 (c)(1),
(2), (4) Date: Oct. 18, 2007

(87) PCT Pub. No.: WO2006/064874

PCT Pub. Date: Jun. 22, 2006

(65) Prior Publication Data

US 2009/0253945 A1 Oct. 8, 2009

(30) Foreign Application Priority Data

Dec. 17, 2004 (JP) ............................. 2004-365507

(51) Int. Cl.
*C07C 29/04* (2006.01)

(52) U.S. Cl. ...................................... 568/896; 568/895
(58) Field of Classification Search ................ 568/895, 568/896
See application file for complete search history.

(56) References Cited

FOREIGN PATENT DOCUMENTS

| JP | 54 27507 | 3/1979 |
|----|----------|--------|
| JP | 54 30104 | 3/1979 |
| JP | 54 30105 | 3/1979 |
| JP | 56 10124 | 2/1981 |
| JP | 60 233024 | 11/1985 |
| JP | 11 193255 | 7/1999 |
| JP | 2005 68150 | 3/2005 |
| WO | 99 33775 | 7/1999 |

*Primary Examiner*—Elvis O Price
(74) *Attorney, Agent, or Firm*—Oblon, Spivak, McClelland, Maier & Neustadt, L.L.P.

(57) ABSTRACT

Disclosed is a method for producing tertiary butyl alcohol through hydration reaction of isobutylene and water in the presence of a cation exchange resin by using a reactor having at least two reactor vessels provided in series. The method is characterized in that a fluid in a reactor vessel at the most downstream side forms a two-liquid phase and the reaction temperature of the reactor vessel is kept at 70° C. or lower, and a fluid in at least one reactor vessel other than the one at the most downstream side forms a homogeneous phase.

3 Claims, 2 Drawing Sheets

METHOD FOR PRODUCING TERTIARY BUTYL ALCOHOL

TECHNICAL FIELD

The present invention relates to a method for producing tertiary butyl alcohol (2-methyl-2-propanol, hereinafter properly expressed as "TBA").

The present application claims the priority of Japanese Patent Application No. 2004-365,507 filed on Dec. 17, 2004, the contents of which are incorporated herein by reference.

BACKGROUND ART

As a conventional method for producing tertiary butyl alcohol, a hydration reaction of isobutylene (2-methylpropene) and water using a catalyst has been known.

In Patent Document 1, tertiary butyl alcohol is described as an assistant for carrying out a hydration reaction by making a hydrocarbon and water into a homogeneous liquid phase.

Further, a method is described in Patent Document 2, in which all of the region of hydration reaction is made into a homogeneous liquid phase and further, a step of separating tertiary butyl alcohol is included in the middle of the process.

In Patent Documents 3, 4, 5 and 6, methods for carrying out reactions in heterogeneous liquid phases are described.

Patent Document 1: Japanese Patent Application Laid-Open No. Sho 56-10,124
Patent Document 2: Japanese Patent Application Laid-Open No. Sho 60-233,024
Patent Document 3: International Publication No. WO 99/33,775
Patent Document 4: Japanese Patent Application Laid-Open No. Sho 54-27,507
Patent Document 5: Japanese Patent Application Laid-Open No. Sho 54-30,104
Patent Document 6: Japanese Patent Application Laid-Open No. Sho 54-30,105

DISCLOSURE OF INVENTION

[Problems to be Solved by the Invention]

Generally, there has been a problem that the reaction rate of the hydration reaction of water and hydrocarbon such as isobutylene is low because the mutual solubility of water and a hydrocarbon such as isobutylene is low and hence a two-liquid phase is formed when these are mixed in a liquid state. Further, there has been a problem that the conversion of isobutylene to TBA (hereinafter expressed as "conversion") is low because the hydration reaction of isobutylene and water is an equilibrium reaction.

There has been a problem in the method described in Patent Document 1 that the conversion is restricted by equilibrium because TBA which is the target product is added to raw materials of the reaction, though the hydration reaction can be carried out in a homogeneous liquid phase.

There has been a problem in the method described in Patent Document 2 that the conversion is restricted by equilibrium because a TBA aqueous solution is also added to the last reactor vessel to make a homogeneous liquid phase, though a higher conversion than the one in the method described in Patent Document 1 can be attained since the hydration reaction is carried out in a homogeneous liquid phase and a TBA aqueous solution is once separated in the middle of the hydration reaction.

There has been a problem in the method described in Patent Document 3 that the conversion is restricted by equilibrium because the reaction fluid changes into a homogeneous liquid phase with the progress of the reaction, though the reaction fluid having a composition at the inlet of the reactor vessel forms heterogeneous liquid phases.

There has been a problem in the methods described in Patent Documents 4, 5 and 6 that the reaction rate of the hydration reaction is low because reactions in all reactor vessels are carried out in heterogeneous liquid phases.

The present invention is provided to solve the above-mentioned problems and the object of the present invention is to improve the conversion of the hydration reaction of isobutylene and water.

[Means for Solving the Problems]

The present inventors have diligently researched the method for producing TBA to solve the above-mentioned problems. As a result, they have found that a conversion obtained when a reaction fluid is made into the state of a two-liquid phase is in some cases larger than the one obtained when the reaction fluid is in the state of a homogeneous liquid phase and thus have completed the present invention.

Namely, the present invention is a method for producing tertiary butyl alcohol through hydration reaction of isobutylene and water in the presence of a cation exchange resin by using a reactor having at least two reactor vessels provided in series, comprising:

making a fluid in a reactor vessel at the most downstream side form a two-liquid phase while keeping a reaction temperature of the reactor vessel at 70° C. or lower; and making a fluid in at least one reactor vessel other than the reactor vessel at the most downstream side form a homogeneous phase.

In the present invention, it is preferable that fluids in all the reactor vessels other than the reactor vessel at the most downstream side be homogeneous phases.

Further, in the present invention, it is preferable that a part of the tertiary butyl alcohol be removed from a reaction liquid taken out from an outlet of a reactor vessel located upstream by one from the reactor vessel at the most downstream side and the resultant reaction liquid in which a part of the tertiary butyl alcohol has been removed be supplied to the reactor vessel at the most downstream side.

[Effects Of The Invention]

According to the present invention, a high conversion can be realized in the hydration reaction of isobutylene, and TBA can be produced effectively.

EXPLANATION OF NUMERALS

Figure 1:
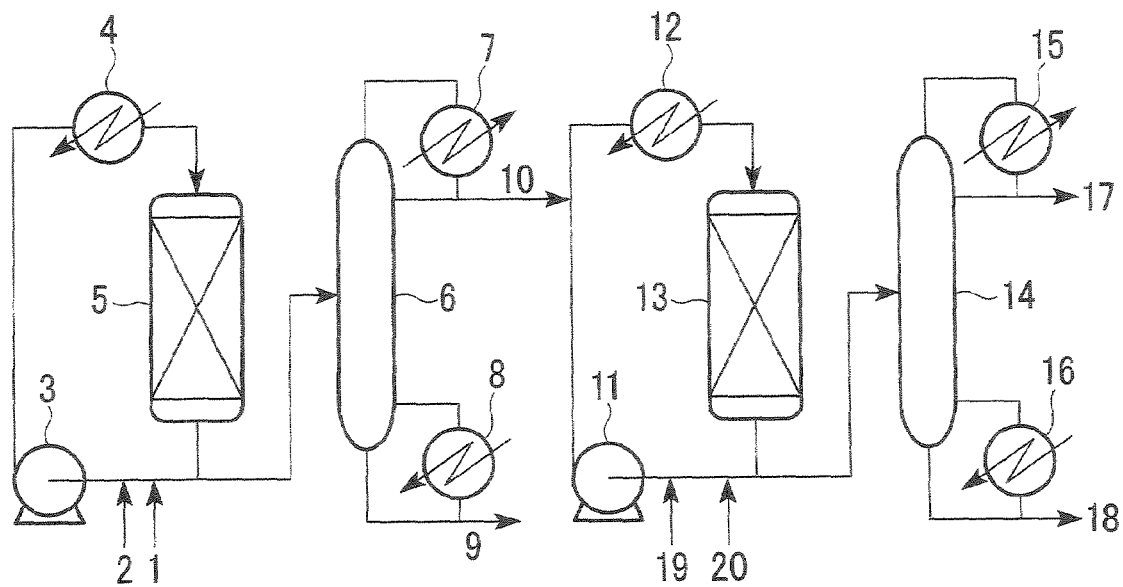
FIG. 1 is a schematic diagram showing an embodiment of a production flow to carry out the method of the present invention.

1: Isobutylene supply port
2: Water supply port
3: Pump
4: Preheater for raw material
5: First reactor vessel 6: TBA aqueous solution separating column
7: Condenser
8: Reboiler
9: TBA aqueous solution
10: Isobutylene or isobutylene-containing hydrocarbon
11: Pump
12: Preheater for raw material
13: Second reactor vessel
14: TBA aqueous solution separating column
15: Condenser
16: Reboiler
17: Unreacted isobutylene or an unreacted isobutylene-containing hydrocarbon
18: TBA aqueous solution
19: TBA supply port
20: Water supply port

BEST MODE FOR CARRYING OUT THE INVENTION

The reactor vessel to be used in the present invention is not particularly limited and any of a stirred-tank type reactor vessel, a fixed-bed type reactor vessel, a column type reactor vessel, and the like can be used. Further, the type of the reaction may be any of a batch type, semibatch type and continuous type. In the reactor in the present invention, the number of the reactor vessels provided in series is 2 or more, preferably 2 to 5. It is preferable in the present invention that all the reactor vessels be provided in series, however, reactor vessels provided in parallel may be used as long as the above-mentioned series condition is fulfilled.

The cation exchange resin to be used in the present invention is preferably a strongly acidic cation-exchange resin. For example, LEWATIT (trade name) manufactured by Bayer AG, AMBERLYST (trade name) manufactured by Rohm and Haas Company and the like can be listed.

The hydration reaction in the present invention means a reaction which produces TBA by a reaction of isobutylene and water. The reaction pressure in the hydration reaction is not particularly limited, however, it is preferably a pressure sufficient to liquefy isobutylene gas or an isobutylene-containing hydrocarbon gas which is used as a raw material. Concretely, the reaction pressure is preferably within the range of 0.2 to 2.0 MPa (gauge pressure, hereinafter expressed in the same way) and more preferably within the range of 0.4 to 1.6 MPa. An inert gas which does not take part in the hydration reaction can be introduced into the reactor vessel to maintain the reaction pressure during the hydration reaction. As the inert gas, nitrogen, argon and the like can be listed.

As the source of isobutylene to be used in the present invention, a mixture which contains isobutylene and other hydrocarbons (hereinafter expressed as "isobutylene-containing hydrocarbon") as well as an enriched isobutylene can also be used. The isobutylene-containing hydrocarbon is preferably used in the form of liquefied gas at the time of the hydration reaction. As hydrocarbons other than isobutylene contained in the isobutylene-containing hydrocarbon, at least one kind selected from hydrocarbons having 4 carbon atoms such as butenes other than isobutylene (such as 1-butene and 2-butene) and butanes (such as n-butane and isobutane) is preferable. The isobutylene-containing hydrocarbon as such can be obtained as a by-product in the case of obtaining ethylene by thermal cracking of naphtha in the presence of steam or as a by-product in the case of catalytic cracking of heavy oil, or as a residue which is obtained by removing butadiene from these by-products. The concentration of isobutylene in the isobutylene-containing hydrocarbon is not particularly limited, however, it is preferably within a range approximately from 5 to 95% by mass and more preferably 10 to 80% by mass. Higher concentration of isobutylene is preferable from the viewpoint of realizing a high reaction rate, but lower concentration of isobutylene is preferable from the viewpoint that it is industrially easily obtainable and cheap.

The water to be used in the reaction according to the present invention is not particularly limited, however, deionized water, distilled water and the like are preferable and deionized water is more preferable. It is preferable that impurities in the water be removed as much as possible because those impurities may cause catalyst deactivation or exert harmful influence on product quality.

In the present invention, the fluid in the reactor vessel RN at the most downstream side forms a two-liquid phase. Further, the fluid in at least one reactor vessel, preferably in all the reactor vessels, other than the reactor vessel RN at the most downstream side, forms a homogeneous phase. To confirm whether the fluid forms a two-liquid phase or a homogeneous phase, it is preferable to sample the liquid in the reactor vessel into a glass pressure container and directly confirm it with visual inspection. In the case that it cannot be confirmed directly, a triangular phase diagram of the three components of TBA, water and either isobutylene or an isobutylene-containing hydrocarbon, such as a triangular phase diagram disclosed in FIG. 2 of Patent Document 2, can be used. According to this patent document, the boundary line between the homogeneous liquid phase and the two-liquid phase is expressed by a line connecting points in the following Table 1 and the composition with which the two-liquid phase is formed is within a region shown by oblique lines in FIG. 3. It is preferable that the proportion of TBA, water and either isobutylene or an isobutylene-containing hydrocarbon, which are introduced into the reaction vessel, be adjusted to fall within the region of FIG. 3 where the two-liquid phase is formed.

TABLE 1

| Water (% by mass) | TBA (% by mass) | Hydrocarbon (% by mass) |
|---|---|---|
| 0 | 0 | 100 |
| 2.2 | 21.6 | 76.2 |
| 6.7 | 48.5 | 44.8 |
| 12.5 | 59.8 | 27.7 |
| 22 | 62.5 | 15.5 |
| 35 | 57.5 | 7.5 |
| 49.8 | 46.5 | 3.7 |
| 100 | 0 | 0 |

In the present invention, at least a part of TBA may be removed from a fluid (a reaction liquid) taken out from an outlet of a reactor vessel other than the reactor vessel RN at the most downstream side by a TBA separation step. The resultant reaction liquid in which a part of the TBA has been removed is supplied to a reactor vessel located adjacent to the foregoing reactor vessel on the downstream side.

In the present invention, it is preferable that at least a part of TBA be removed from a reaction liquid taken out from an outlet of a reactor vessel located upstream by one from the reactor vessel RN at the most downstream side and the resultant reaction liquid in which a part of the TBA has been removed be supplied to the reactor vessel RN at the most downstream side. By doing so, it is possible to more easily change the fluid in the reactor vessel RN at the most downstream side into a two-liquid phase.

The fluid at the outlet of the reactor vessel RN contains unreacted isobutylene. In the case that TBA with higher purity is needed industrially, it is preferable that TBA be removed from the reaction liquid in the reactor vessel RN at the most downstream side by a TBA separation step. The purity of the TBA to be obtained in this TBA separation step is not particularly limited as long as it satisfies the purity necessary for a step in which the TBA is used.

A separating device to be used in the TBA separation step of the present reaction is not particularly limited and a distillation device, an extracting device, a membrane separating device, and the like can be used. Among them, the distillation devices such as a distillation column and a flash drum are preferable. The type of the distillation column is not particularly limited and a plate column or a packed column may be used, however, a plate column is preferable. The number of steps of the TBA separation can be determined in consideration of the cost of the device.

In the present invention, the reaction temperature of the reactor vessel R2 (including the reactor vessel RN) in which the fluid forms a two-liquid phase is preferably 70° C. or lower and more preferably within the range of 45 to 65° C. In the case that the number of the reactor vessel R2 in which the fluid forms a two-liquid phase is 2 or more, it is preferable that the reaction temperatures of all the reactor vessels R2 be set at 70° C. or lower, however, it is possible that the reaction temperatures of only a part of the reactor vessels R2 be set at 70° C. or lower. When the reaction temperature is 70° C. or lower, the equilibrium constant of the chemical equilibrium in the present reaction in the case of a two-liquid phase fluid is larger than that in the case of a homogeneous phase fluid. In other words, the conversion at the time of the chemical equilibrium becomes higher in the case of the reaction in the two-liquid phase fluid. The difference between the equilibrium constant in the case of the two-liquid phase fluid and the one in the case of the homogeneous phase fluid becomes larger as the temperature becomes lower in the region of 70° C. or lower, however, when the temperature becomes excessively low, a sufficient reaction rate cannot be realized. When the reaction temperature is higher than 70° C., the equilibrium constant in the case of the two-liquid phase fluid and the one in the case of the homogeneous phase fluid become nearly the same and the conversions at the time of the chemical equilibrium also become nearly the same. The reason why the equilibrium constant in the case of the two-liquid phase fluid becomes larger than the one in the case of the homogeneous phase fluid is not clear. However, when the equilibrium conversion (the equilibrium constant) is determined experimentally by using a batch type reactor, the following phenomenon is confirmed that there is a borderline at 70° C. below which the equilibrium conversion in the state of the two-liquid phase conspicuously exceeds the one in the state of the homogeneous phase.

The reaction temperatures of the other reactor vessels are not particularly limited, however, these are preferably within the range of 25 to 100° C. and more preferably 45 to 80° C. Irrespective of the phase state of the fluid, a higher reaction temperature is preferable to realize a sufficient reaction rate but a lower reaction temperature is preferable to suppress dimerization, trimerization of isobutylene or a formation of other impurities throughout the present reaction.

In the present invention, by changing the fluid in the reactor vessel RN at the most downstream side into a two-liquid phase and keeping the reaction temperature of the reactor vessel at 70° C. or lower, the phenomenon that the conversion in the two-liquid phase becomes higher than the one in the homogeneous phase can be effectively used, and hence the overall conversion in the process can be more improved than ever before.

In the present invention, the method to change a fluid in a reactor vessel into a homogeneous phase is not particularly limited, however for example, a method in which a part of the fluid at the outlet of the reactor vessel or a part of TBA separated in the TBA separation step is circulated into the inlet of the reactor vessel can be listed. Further, a method in which TBA additionally prepared is introduced into the inlet of the reactor vessel, a method in which a reaction solvent (sulfones, ketones, ethers, organic carboxylic acids, or the like) which will be mentioned later is introduced, and the like can be listed. Among them, the method in which a part of the fluid at the outlet of the reactor vessel or a part of TBA separated in the TBA separation step is circulated is preferable.

In the present invention, a solvent may be present when the reaction is carried out. The solvent is not particularly limited, however, sulfones, ketones, ethers and organic carboxylic acids are preferable. As the solvents of sulfones, for example, sulfolane, 2-methyl sulfolane, 3-methyl sulfolane, 3-propyl sulfolane, 3-butyl sulfolane, dimethyl sulfone, diethyl sulfone, methyl ethyl sulfone, dipropyl sulfone, sulfonal and trional can be listed. As the solvents of ketones, for example, acetone, methyl ethyl ketone, methyl-n-propyl ketone, methyl-n-butyl ketone, methyl-isobutyl ketone, methyl-n-amyl ketone, methyl-n-hexyl ketone, diethyl ketone, ethyl-n-butyl ketone, di-n-propyl ketone, di-isobutyl ketone and cyclohexane can be listed. As the solvents of ethers, for example, 1,4-dioxane, trioxane, tetrahydrofuran and tetrahydropyran can be listed. As the solvents of organic carboxylic acids, for example, including carboxylic acid anhydrides, acetic acid, acetic anhydride, propionic acid, propionic anhydride, butyric acid and isobutyric acid can be listed. When the solvent is used, the amount of use of the solvent is not particularly limited. However, it is preferable that the amount of the solvent to be used be determined according to the phase state of the reaction fluid. Generally, the amount of the solvent to be used is preferably within the range of 0.1 to 1.0 mol with respect to 1 mol of isobutylene.

In the present invention, it is preferable that a part of TBA separated in the TBA separation step or a part of the fluid at the outlet of the reactor vessel be supplied to the inlet of the reactor vessel R2 in which the fluid forms a two-liquid phase as long as the fluid in the reactor vessel is within the region in which a two-liquid phase is formed. This is because the larger molar ratio of TBA even within the region in which a two-liquid phase is formed can make the solubility of isobutylene to water higher and hence can make reaction rate larger.

Hereinafter, the present invention will be explained by way of FIG. 1. FIG. 1 is an embodiment of the present invention, and the present invention is not restricted at all by FIG. 1.

Isobutylene or an isobutylene-containing hydrocarbon which is a raw material is supplied from isobutylene supply port 1 and water is supplied from water supply port 2, respectively. A part of the fluid at the outlet of first reactor vessel 5 is circulated into the first reactor vessel through pump 3. A part of the fluid at the outlet of the first reactor vessel 5 is separated into isobutylene or an isobutylene-containing hydrocarbon 10 and TBA aqueous solution 9 through TBA aqueous solution separating column 6. The isobutylene or isobutylene-containing hydrocarbon 10 is supplied to a part of a fluid at an outlet of second reactor vessel 13, which is circulated through pump 11. A part of the fluid at the outlet of the second reactor vessel 13 is supplied to TBA aqueous solution separating column 14 and separated into unreacted isobutylene or an unreacted isobutylene-containing hydrocarbon 17 and TBA aqueous solution 18. Further, the TBA aqueous solutions 9 and 18 can be circulated back to inlets of the first reactor vessel 5 and the second reactor vessel 13, respectively, though these are not shown in the figure.

EXAMPLES

In the examples, a strongly acidic cation-exchange resin (a strongly acidic macroporous ion-exchange resin: LEWATIT K2621 manufactured by Bayer AG, exchange capacity: 1.5 meq/ml) was used as a catalyst.

For the analysis of hydrocarbons and water, which are raw materials, and TBA produced, a gas chromatograph equipped with a capillary column was used. The conversion of isobutylene to TBA (hereinafter expressed as "conversion") and the equilibrium constant were calculated by the following equations.

Conversion (%)={number of moles of isobutylene consumed/number of moles of isobutylene supplied}×100

Equilibrium constant (l/mol)=mole concentration of TBA (mol/l)/{mole concentration of isobutylene (mol/l)×mole concentration of water (mol/l)}

(Equilibrium Constant in a Homogeneous Phase)

Isobutylene, isobutane, water, TBA and a catalyst were charged into a 1 L glass-autoclave equipped with a stirrer. Stirring of the system was started at a stirring rate of 300 rpm and heating of the system was started by an equipped electric heater. After the system reached a predetermined temperature, the gas phase of the autoclave was periodically sampled and the ratio of isobutylene/isobutane in the gas was analyzed to calculate the conversion. When the conversion becomes nearly constant and hence the system reached equilibrium, the experiment was finished. The equilibrium constant was calculated from the composition in the autoclave at the time of equilibrium. The experimental conditions and the experimental results are shown in Table 2.

TABLE 2

| | Reaction temperature (° C.) | 55.4 | 65.6 | 70.2 |
|---|---|---|---|---|
| Charge stock composition (mol) | Isobutylene | 0.56 | 0.45 | 0.58 |
| | Isobutane | 0.27 | 0.21 | 0.28 |
| | Water | 1.43 | 1.43 | 1.43 |
| | TBA | 2.11 | 1.98 | 2.11 |
| | Catalyst (ml) | 15 | 20 | 16 |
| | State of liquid phase | Homogeneous phase | Homogeneous phase | Homogeneous phase |
| Reaction end point composition (mol) | Isobutylene | 0.23 | 0.14 | 0.33 |
| | Isobutane | 0.27 | 0.21 | 0.28 |
| | Water | 1.09 | 1.12 | 1.18 |
| | TBA | 2.44 | 2.29 | 2.35 |
| | State of liquid phase | Homogeneous phase | Homogeneous phase | Homogeneous phase |
| | Liquid volume (L) | 0.31 | 0.29 | 0.33 |
| Time for attaining the equilibrium (hrs) | | 5.5 | 3.5 | 2 |
| Equilibrium constant (l/mol) | | 3.05 | 2.32 | 1.94 |

(Equilibrium Constant in a Heterogeneous Phase)

A device in which a 1.8 L glass-autoclave equipped with a stirrer and a stainless steel fixed-bed reactor (with an inside diameter of 40 mm and a height of 250 mm) were connected in series was used. An isobutylene-containing hydrocarbon, water and TBA were charged into the autoclave and a catalyst was charged in the fixed-bed reactor. Stirring of the system was started at a stirring rate of 300 rpm and heating of the system was started by an equipped electric heater while the liquid in the autoclave was supplied to the fixed-bed reactor with a pump. The liquid thus supplied to the fixed-bed reactor was contacted with the catalyst and returned to the autoclave. After the system reached a predetermined temperature, the gas phase in the autoclave was periodically sampled and the ratio of isobutylene/isobutane in the gas was analyzed to calculate the conversion. When the conversion becomes nearly constant and hence the system reached equilibrium, the experiment was finished. The equilibrium constant was calculated from the composition in the autoclave at the time of equilibrium. The experimental conditions and the experimental results are shown in Table 3.

TABLE 3

| Reaction temperature (° C.) | | 50.1 | 59.8 | 69.2 |
|---|---|---|---|---|
| Charge stock composition (mol) | Isobutylene | 4.75 | 2.51 | 4.52 |
| | Isobutane | 7.60 | 7.20 | 7.24 |
| | Water | 6.44 | 4.26 | 6.43 |
| | TBA | 0.30 | 2.50 | 0.30 |
| | Catalyst (ml) | 88.0 | 88.0 | 88.0 |
| | State of liquid phase | Two-liquid phase | Two-liquid phase | Two-liquid phase |
| Reaction end point composition (mol) | Isobutylene | 0.52 | 0.74 | 1.06 |
| | Isobutane | 7.59 | 7.21 | 7.24 |
| | Water | 2.20 | 2.49 | 2.97 |
| | TBA | 4.53 | 4.26 | 3.76 |
| | State of liquid phase | Two-liquid phase | Two-liquid phase | Two-liquid phase |
| | Liquid volume (L) | 1.30 | 1.28 | 1.31 |
| Time for attaining the equilibrium (hrs) | | 107 | 23.5 | 20 |
| Equilibrium constant (l/mol) | | 5.17 | 2.94 | 1.57 |

Example 1

Figure 2:
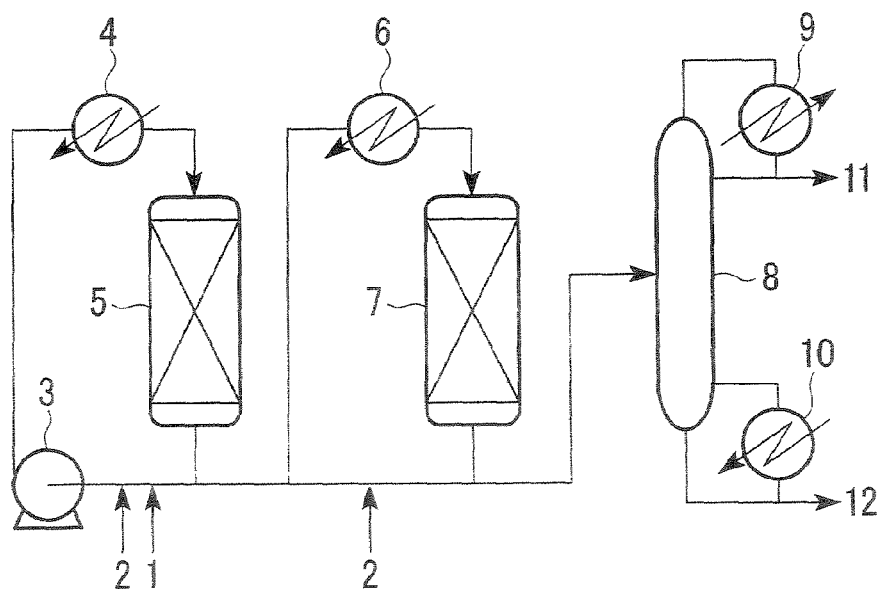
FIG. 2 is another schematic diagram showing another embodiment of a production flow to carry out the method of the present invention.
Figure 3:
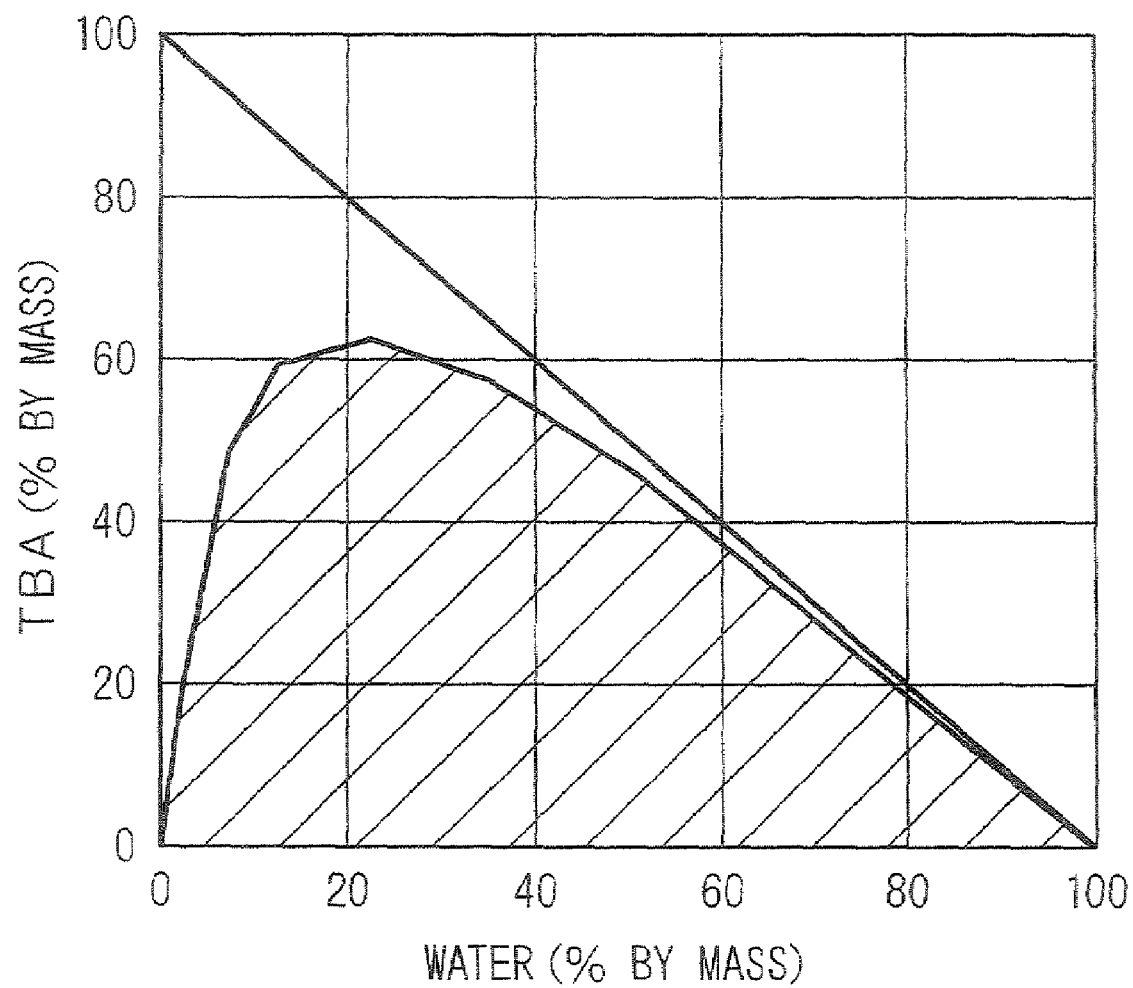
FIG. 3 is a diagram showing a region in which a two-liquid phase is formed.

The overall conversion of the multistage reactor shown in FIG. 2 is calculated by using the relation of equilibrium constants and temperatures obtained by the foregoing experiments. TBA is added in a first stage reactor vessel to carry out a reaction in a homogeneous liquid phase. Water is added in a second stage reactor vessel to carry out a reaction in a heterogeneous liquid phase. The reaction temperature is presumed to be 50° C., and the equilibrium constant in the homogeneous liquid phase and the one in the heterogeneous liquid phase are estimated to be 4.22 (l/mol) and 5.25 (l/mol), respectively. The calculated results are shown in Table 4. FIG. 3 is used to judge the state of the liquid phase.

TABLE 4

| | Charge stock composition | Added TBA | After the first stage reaction | Added water | After the second stage reaction |
|---|---|---|---|---|---|
| (g) | | | | | |
| Isobutylene | 10 | — | 2.0 | — | 1.1 |
| Isobutane | 20 | — | 20.0 | — | 20.0 |
| Water | 5 | — | 2.4 | 2 | 4.1 |
| TBA | — | 10 | 20.5 | — | 21.8 |

TABLE 4-continued

| | Charge stock composition | Added TBA | After the first stage reaction | Added water | After the second stage reaction |
|---|---|---|---|---|---|
| (mol) | | | | | |
| Isobutylene | 0.18 | — | 0.04 | — | 0.02 |
| Isobutane | 0.34 | — | 0.34 | — | 0.34 |
| Water | 0.28 | — | 0.14 | 0.11 | 0.23 |
| TBA | — | 0.13 | 0.28 | — | 0.29 |
| State of liquid phase | — | — | Homogeneous phase | — | Heterogeneous phase |
| Conversion | — | — | 79.7% | — | 89.3% |
| Equilibrium constant | — | — | 4.22 | — | 5.25 |

Example 2

Calculation is carried out with the same condition as in Example 1 except that a separating step, assuming a distillation column, is provided after the first stage reactor vessel as shown in FIG. 1. In the separating step, calculation is carried out on the assumption that TBA and water are distilled out with an azeotropic mixture (TBA: 86 mass %, water: 14 mass %). A flowchart of the process is shown in FIG. 1 and the calculated results are shown in Table 5.

TABLE 5

| | Charge stock composition | Added TBA | After the first stage reaction | Separation TBA/water | Added water | After the second reaction |
|---|---|---|---|---|---|---|
| (g) | | | | | | |
| Isobutylene | 10 | — | 2.0 | — | — | 0.8 |
| Isobutane | 20 | — | 20.0 | — | — | 20.0 |
| Water | 5 | — | 2.4 | 2.4 | 1.5 | 1.1 |
| TBA | — | 10 | 20.5 | 15.0 | — | 7.1 |
| (mol) | | | | | | |
| Isobutylene | 0.18 | — | 0.04 | — | — | 0.01 |
| Isobutane | 0.34 | — | 0.34 | — | — | 0.34 |
| Water | 0.28 | — | 0.14 | 0.14 | 0.08 | 0.06 |
| TBA | — | 0.13 | 0.28 | 0.20 | — | 0.10 |
| State of liquid phase | — | — | Homogeneous phase | — | — | Heterogeneous phase |

TABLE 5-continued

|  | Charge stock composition | Added TBA | After the first stage reaction | Separation TBA/water | Added water | After the second reaction |
|---|---|---|---|---|---|---|
| Conversion | — | — | 79.7% | — | — | 91.9% |
| Equilibrium constant | — | — | 4.22 | — | — | 5.25 |

Comparative Example 1

Calculation is carried out with the same condition as in Example 2 except that the amounts of added water and TBA to be supplied to the second stage reactor vessel are changed to make the inside of the second stage reactor vessel a homogeneous liquid phase. The calculated results are shown in Table 6.

TABLE 6

|  | Charge stock composition | Added TBA | After the first stage reaction | Separation TBA/water | Added water and TBA | After the second stage reaction |
|---|---|---|---|---|---|---|
| (g) | | | | | | |
| Isobutylene | 10 | — | 2.0 | — | — | 1.8 |
| Isobutane | 20 | — | 20.0 | — | — | 20.0 |
| Water | 5 | — | 2.4 | 2.4 | 1 | 0.9 |
| TBA | — | 10 | 20.5 | 15.0 | 4 | 9.8 |
| (mol) | | | | | | |
| Isobutylene | 0.18 | — | 0.04 | — | — | 0.03 |
| Isobutane | 0.34 | — | 0.34 | — | — | 0.34 |
| Water | 0.28 | — | 0.14 | 0.14 | 0.06 | 0.05 |
| TBA | — | 0.13 | 0.28 | 0.20 | 0.05 | 0.13 |
| State of liquid phase | — | — | Homogeneous phase | — | — | Heterogeneous phase |
| Conversion | — | — | 79.7% | — | — | 81.7% |
| Equilibrium constant | — | — | 4.22 | — | — | 4.22 |

INDUSTRIAL APPLICABILITY

According to the present invention, a high conversion can be obtained in the hydration reaction of isobutylene and water, and TBA can be produced effectively.

The invention claimed is:

1. A method for producing tertiary butyl alcohol through hydration reaction of isobutylene and water in the presence of a cation exchange resin by using a reactor having at least two reactor vessels provided in series, comprising:
    making a fluid in a reactor vessel at the most downstream side form a two-liquid phase while keeping a reaction temperature of the reactor vessel at 70° C. or lower; and
    making a fluid in at least one reactor vessel other than the reactor vessel at the most downstream side form a homogeneous phase.

2. The method for producing tertiary butyl alcohol of claim 1, wherein fluids in all the reactor vessels other than the reactor vessel at the most downstream side are homogeneous phases.

3. The method for producing tertiary butyl alcohol of claim 1 or 2, wherein a part of the tertiary butyl alcohol is removed from a reaction liquid taken out from an outlet of a reactor vessel located upstream by one from the reactor vessel at the most downstream side and the resultant reaction liquid in which a part of the tertiary butyl alcohol has been removed is supplied to the reactor vessel at the most downstream side.

* * * * *